United States Patent
Ono

(10) Patent No.: US 9,901,924 B2
(45) Date of Patent: Feb. 27, 2018

(54) FLUID HANDLING DEVICE, FLUID HANDLING METHOD, AND FLUID HANDLING SYSTEM

(75) Inventor: Koichi Ono, Saitama (JP)

(73) Assignee: Enplas Corporation, Saitama (JP)

( * ) Notice: Subject to any disclaimer, the term of this patent is extended or adjusted under 35 U.S.C. 154(b) by 147 days.

(21) Appl. No.: 14/131,933

(22) PCT Filed: Jul. 6, 2012

(86) PCT No.: PCT/JP2012/004417
§ 371 (c)(1),
(2), (4) Date: Jan. 10, 2014

(87) PCT Pub. No.: WO2013/008442
PCT Pub. Date: Jan. 17, 2013

(65) Prior Publication Data
US 2014/0166113 A1    Jun. 19, 2014

(30) Foreign Application Priority Data
Jul. 14, 2011 (JP) ................................ 2011-155679

(51) Int. Cl.
*F15C 1/00* (2006.01)
*B01L 3/00* (2006.01)
(Continued)

(52) U.S. Cl.
CPC ....... *B01L 3/50273* (2013.01); *B01J 19/0093* (2013.01); *B01L 3/502738* (2013.01);
(Continued)

(58) Field of Classification Search
CPC .......... F15C 1/04; F17D 1/18; B01L 3/50273; B01L 3/502738; B01L 2300/0816;
(Continued)

(56) References Cited

U.S. PATENT DOCUMENTS 4,278,110 A * 7/1981 Price et al. ............... 137/805
4,426,451 A * 1/1984 Columbus ......... B01L 3/502738
138/44
(Continued)

FOREIGN PATENT DOCUMENTS

EP         2138233      * 12/2009 ............... B01L 3/00
JP     2005-246203 A     9/2005
(Continued)

OTHER PUBLICATIONS

Kurowski et al., EP 2138233, Dec. 30, 2009, machine translation.*

*Primary Examiner* — Minh Le
(74) *Attorney, Agent, or Firm* — Brundidge & Stanger, P.C.

(57) ABSTRACT

A fluid handling device (100) comprises: a first channel (130); a second channel (140); a communication section (150); an air introduction path (160); and an air reservoir (190). The first enamel (130) and the second channel (140) are channels through which a fluid (210) can move by capillary action. The communication section (150) connects the first channel (130) and the second channel (140) with each other, and has a cross-sectional area smaller than the cross-sectional area of the second channel (140). The air introduction path (160) communicates with the first channel (130). The air reservoir (190) communicates with the air introduction path (160).

4 Claims, 17 Drawing Sheets

(51) Int. Cl.
*B01J 19/00* (2006.01)
*G01N 35/00* (2006.01)

(52) U.S. Cl.
CPC .......... *B01J 2219/0086* (2013.01); *B01J 2219/00783* (2013.01); *B01J 2219/00833* (2013.01); *B01J 2219/00885* (2013.01); *B01L 2300/0816* (2013.01); *B01L 2300/0867* (2013.01); *B01L 2300/18* (2013.01); *B01L 2400/0655* (2013.01); *B01L 2400/0688* (2013.01); *G01N 2035/00158* (2013.01); *Y10T 137/0318* (2015.04); *Y10T 137/85938* (2015.04)

(58) Field of Classification Search
CPC ......... B01L 2300/0867; B01L 2300/18; B01L 2400/0655; B01L 2400/0688; B01J 19/0093; B01J 2219/00783; B01J 2219/00833; B01J 2219/0086; B01J 2219/00885; G01N 2035/00158
USPC .................. 137/829, 833, 825, 828; 417/479
See application file for complete search history.

(56) References Cited

U.S. PATENT DOCUMENTS

| | | | | |
|---|---|---|---|---|
| 4,949,742 A * | 8/1990 | Rando et al. | | 137/13 |
| 5,304,487 A * | 4/1994 | Wilding et al. | | 435/29 |
| 5,700,245 A * | 12/1997 | Sancoff | | A61M 5/14593 222/399 |
| 5,863,502 A * | 1/1999 | Southgate | | B01J 19/0046 422/417 |
| 6,453,928 B1 * | 9/2002 | Kaplan et al. | | 137/14 |
| 6,505,648 B1 * | 1/2003 | Gergely et al. | | 137/828 |
| 6,520,197 B2 * | 2/2003 | Deshmukh et al. | | 137/3 |
| 6,601,613 B2 * | 8/2003 | McNeely et al. | | 137/833 |
| 6,843,263 B2 * | 1/2005 | Kuo | | F04B 43/02 137/14 |
| 6,921,253 B2 * | 7/2005 | Shuler | | F04B 43/043 417/413.2 |
| 7,069,943 B2 * | 7/2006 | Gilbert et al. | | 137/14 |
| 7,156,117 B2 * | 1/2007 | Bohm | | 137/14 |
| 8,061,566 B2 * | 11/2011 | LaFlamme | | A47K 7/03 222/207 |
| 9,173,994 B2 * | 11/2015 | Ziaie | | A61M 5/14248 |
| 9,315,663 B2 * | 4/2016 | Appleby | | C08L 63/00 |
| 2002/0081222 A1 * | 6/2002 | Karp | | F04B 43/043 417/507 |
| 2002/0114715 A1 * | 8/2002 | Yoon | | F04B 17/00 417/393 |
| 2003/0196714 A1 * | 10/2003 | Gilbert et al. | | 137/828 |
| 2004/0007275 A1 * | 1/2004 | Hui Liu et al. | | 137/828 |
| 2004/0064110 A1 * | 4/2004 | Forsell | | A61M 5/1428 604/288.01 |
| 2004/0121481 A1 * | 6/2004 | Stroup | | B01F 11/0065 436/165 |
| 2006/0034727 A1 | 2/2006 | Takamura et al. | | |
| 2006/0076068 A1 * | 4/2006 | Young | | B01F 5/0683 137/829 |
| 2006/0289309 A1 | 12/2006 | Fukuzawa et al. | | |
| 2009/0155927 A1 | 6/2009 | Higashino et al. | | |
| 2010/0124624 A1 * | 5/2010 | Tanaami | | B01L 3/5027 428/34.1 |
| 2010/0171719 A1 * | 7/2010 | Craig | | G06F 3/0202 345/173 |
| 2010/0171720 A1 * | 7/2010 | Craig | | G06F 3/0202 345/173 |
| 2010/0260626 A1 * | 10/2010 | Fajolle | | B01L 3/50273 417/413.2 |
| 2011/0135546 A1 * | 6/2011 | Kurowski | | B01L 3/502707 422/502 |
| 2011/0147408 A1 | 6/2011 | Nakajima et al. | | |

FOREIGN PATENT DOCUMENTS

| | | |
|---|---|---|
| JP | 2006-053090 A | 2/2006 |
| JP | 2007-232172 A | 9/2007 |
| JP | 2011-025127 A | 2/2011 |
| WO | 2007/052471 A1 | 5/2007 |
| WO | 2008/059848 A1 | 5/2008 |
| WO | 2009/136600 A1 | 11/2009 |

* cited by examiner

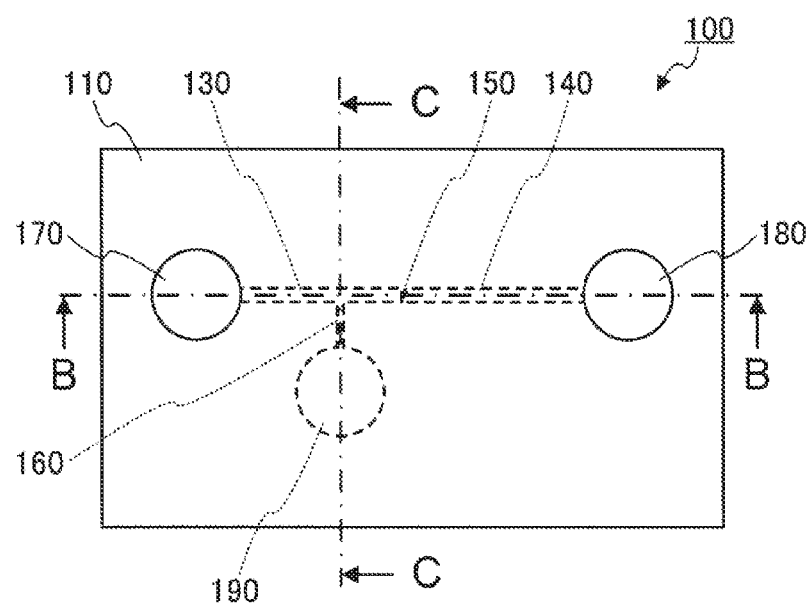
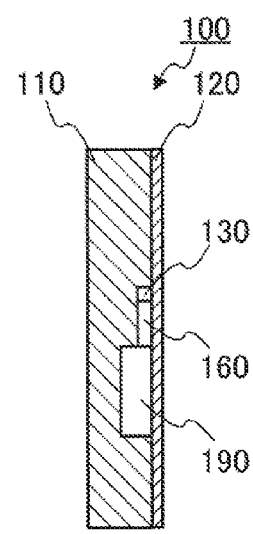
FIG. 1A
FIG. 1C
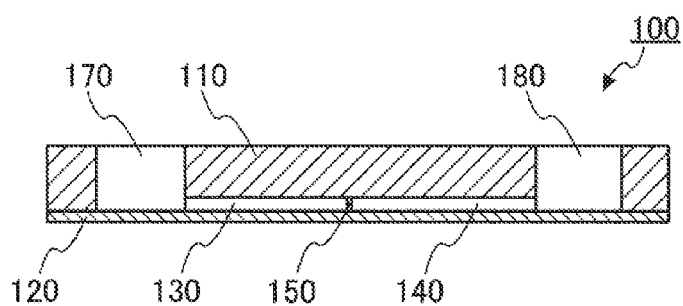
FIG. 1B

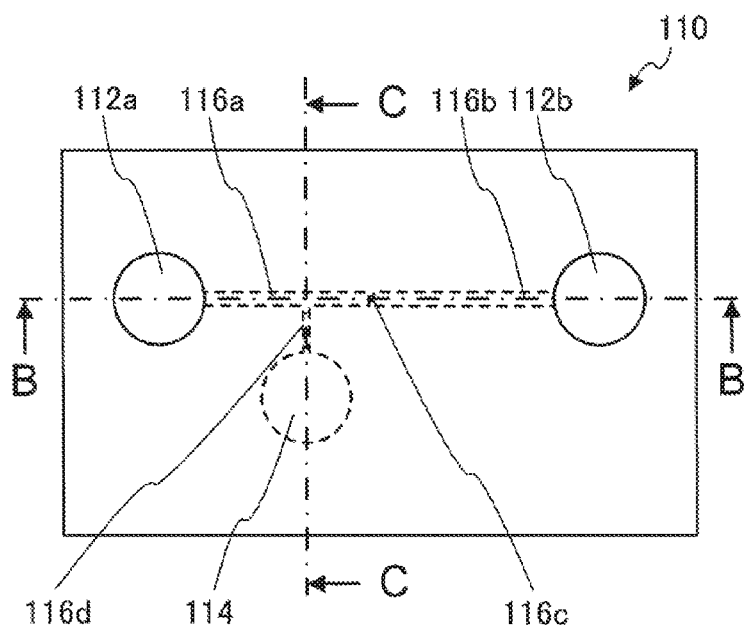
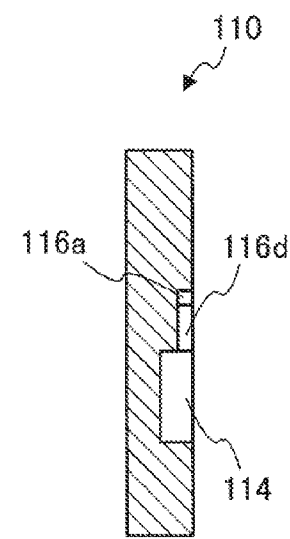
FIG. 2A  FIG. 2C
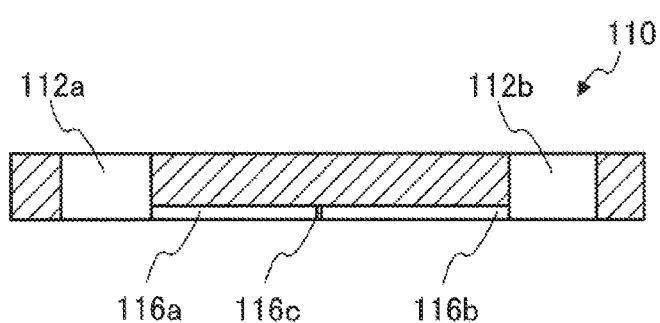
FIG. 2B

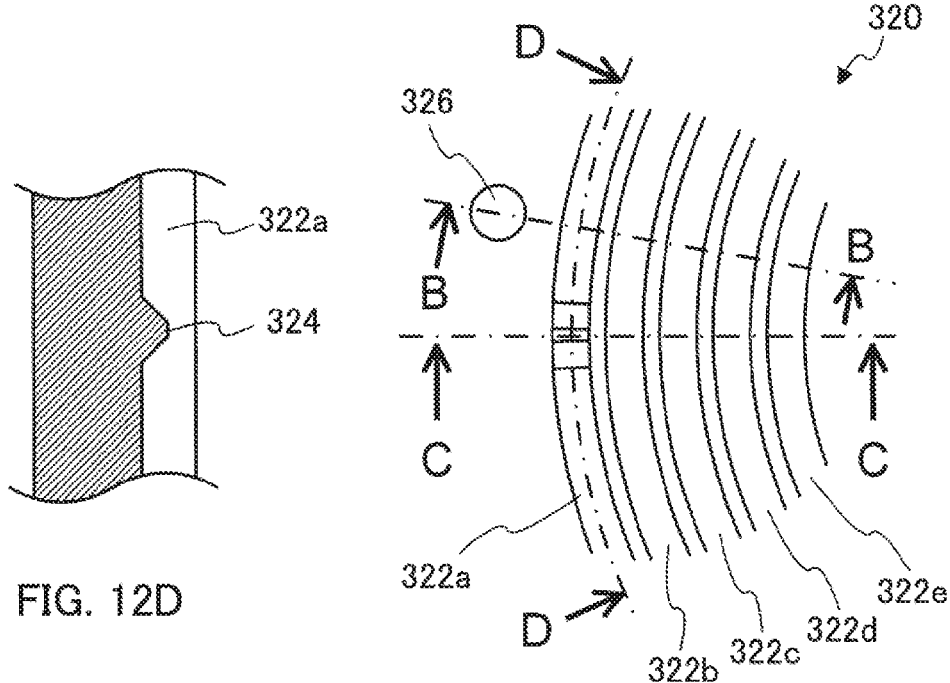
FIG. 12D
FIG. 12A
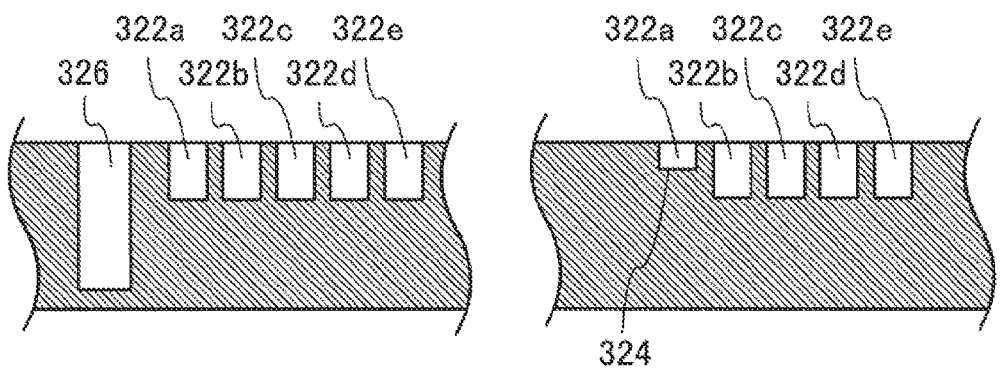
FIG. 12B
FIG. 12C

FLUID HANDLING DEVICE, FLUID HANDLING METHOD, AND FLUID HANDLING SYSTEM

TECHNICAL FIELD

The present invention relates to a fluid handling device and a fluid handling method which are used for analysis, processing or the like of a liquid sample, and a fluid handling system having the fluid handling device.

BACKGROUND ART

In recent years, in order to perform accurate and fast analysis of trace amounts of materials such as proteins or nucleic acids, microchannel chips have been used. The microchannel chips have an advantage of requiring smaller amounts of reagent and sample and thus are expected to be used in various applications including clinical inspection, food inspection, and environmental inspection.

As a technology in order to automate the process using the microchannel chip, a microchannel chip including a valve structure is disclosed (for example, see PTL 1).

PTL 1 discloses a microchannel chip including a microvalve apparatus which stops flow of liquid inside a liquid channel by supplying air inside the liquid channel. In the microchannel chip described in PTL 1, a valve channel communicating with the liquid channel is formed. The valve channel is connected to a fluid control mechanism (a pump or a syringe) provided outside. When the air is supplied from the valve channel to the liquid channel, an air bubble is formed inside the liquid channel, so that the liquid cannot flow inside the liquid channel. As described above, in the microchannel chip described in PTL 1, the flow of the liquid in the liquid channel can be stopped by supplying the air inside the liquid channel using the fluid control mechanism provided outside.

CITATION LIST

Patent Literature

PTL 1
Japanese Patent Application Laid-Open No. 2007-232177

SUMMARY OF INVENTION

Technical Problem

However, the microchannel chip described in PTL 1 has the disadvantage of allowing the apparatus increased in size.

That is, in the microchannel chip described in PTL 1, in order to control the liquid flow inside the liquid channel, the fluid control mechanism (the pump and the syringe) must be installed outside. Therefore, when an automatic analysis apparatus using the microchannel chip described in PTL 1 is manufactured, the apparatus is increased in size.

An object of the present invention is to provide a fluid handling device and a fluid handling method which can easily control fluid flow inside a channel without providing a large-scale apparatus outside. Another object of the present invention is to provide a fluid handling system having the fluid handling device.

Solution to Problem

A fluid handling device of the present invention includes: a first channel through which a fluid can move by capillary action; a second channel through which the fluid can move by the capillary action; a communication section that connects the first channel and the second channel with each other, and has a cross-sectional area smaller than a cross-sectional area of the second channel; an air introduction path communicating with the first channel; and an air reservoir communicating with the air introduction path.

A fluid handling method of the present invention, in which a fluid is handled using the fluid handling device described above, includes: introducing the fluid into the first channel and the communication section; pushing some of the fluid inside the first channel and the communication section to the second channel by introducing some of the air inside the air reservoir into the first channel through the air introduction path; and moving the fluid in the second channel by the capillary action.

A fluid handling system of the present invention includes: the fluid handling device described above; and a valve opening portion that presses the air reservoir of the fluid handling device from outside or heats the air inside the air reservoir of the fluid handling device.

Advantageous Effects of Invention

According to the present invention, it is possible to easily control the flow of the fluid inside the channels of the fluid handling device without providing a large-scale apparatus outside.

BRIEF DESCRIPTION OF DRAWINGS

FIG. 1A is a plan view of a microchannel chip, FIG. 1B is a cross-sectional view of the microchannel chip taken along line B-B illustrated in FIG. 1A and FIG. 1C is a cross-sectional view of the microchannel chip taken along line C-C illustrated in FIG. 1A;

FIG. 2A is a plan view of a chip main body, FIG. 2B is a cross-sectional view of the chip main body taken along line B-B illustrated in FIG. 2A and FIG. 2C is a cross-sectional view of the chip main body taken along line C-C illustrated in FIG. 2A;

FIG. 12A is an enlarged plan view of an area A indicated by a dashed line in FIG. 11A, FIG. 12B is a cross-sectional view of the area A taken along line B-B illustrated in FIG. 12A, FIG. 12C is a cross-sectional view of the area A taken along line C-C illustrated in FIG. 12A and FIG. 12D is a cross-sectional view of the area A taken along line D-D illustrated in FIG. 12A;

DESCRIPTION OF EMBODIMENTS

Hereinafter, embodiments of the present invention will be described in detail with reference to the drawings. As used herein, "film" means a thin plate-shaped member. For example, "resin film" includes a resin thin plate in addition to a resin thin film.

Configuration of Microchannel Chip

First, as a representative example of a fluid handling device of the present invention, a microchannel chip will be described.

FIGS. 1A to 1C illustrate a configuration of microchannel chip 100 according to an embodiment of the present invention. FIG. 1A is a plan view of microchannel chip 100, FIG. 1B is a cross-sectional view of microchannel chip 100 taken along line B-B illustrated in FIG. 1A and FIG. 1C is a cross-sectional view of microchannel chip 100 taken along line C-C illustrated in FIG. 1A.

FIGS. 2A to 2C illustrate a configuration of chip main body 110 of microchannel chip 100. FIG. 2A is a plan view of chip main body 110, FIG. 2B is a cross-sectional view of chip main body 110 taken along line B-B illustrated in FIG. 2A and FIG. 2C is a cross-sectional view of chip main body 110 taken along line C-C illustrated in FIG. 2A.

Figure 3A:
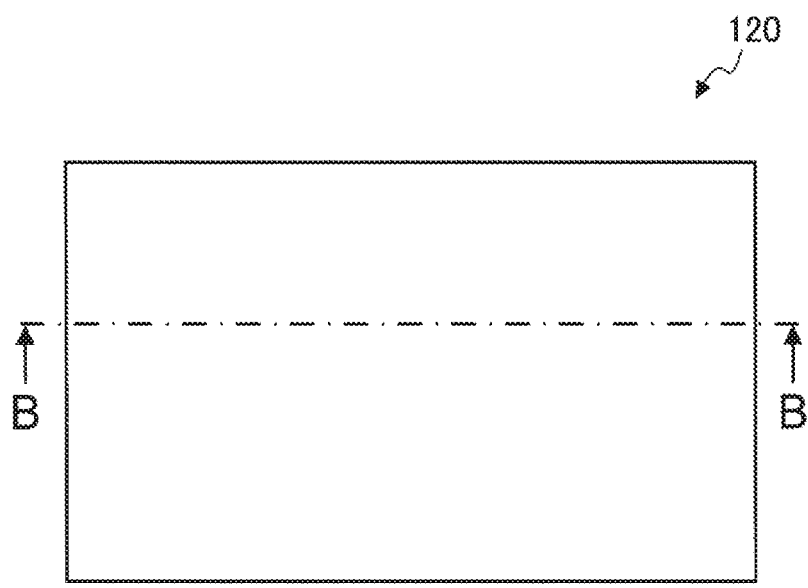
FIG. 3A is a plan view of a resin film and FIG. 3B is a cross-sectional view of the resin film taken along line B-B illustrated in FIG. 3A.
Figure 3B:
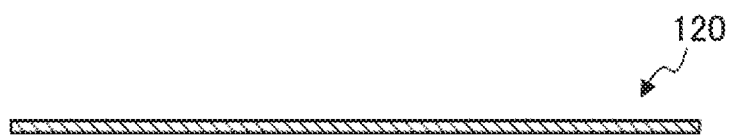

FIGS. 3A and 3B illustrate a configuration of resin film 120 of microchannel chip 100. FIG. 3A is a plan view of resin film 120 and FIG. 3B is a cross-sectional view of resin film 120 taken along line B-B illustrated in FIG. 3A.

Figure 4:
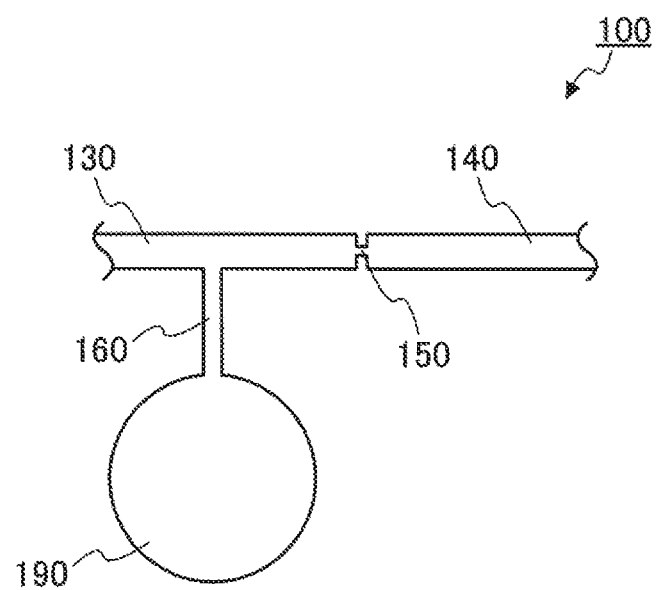
FIG. 4 is a partially enlarged plan view of the microchannel chip.

FIG. 4 is a partially enlarged plan view of microchannel chip 100.

As illustrated in FIGS. 1A to 1C, microchannel chip 100 is a plate-shaped device having two bottomed recesses (first recess 170 and second recess 180) and one enclosed space (air reservoir 190). First recess 170 and second recess 180 communicate with each other by channels (first channel 130, second channel 140 and communication section 150). An reservoir 190 communicates with first channel 130 through air introduction path 160.

First recess 170 serves as an introduction port for introducing fluid into the channels. In contrast, second recess 180 serves as an outlet port for taking out the fluid from the inside of the channel. As described below, air reservoir 190 is formed so as to reduce a capacity thereof when being pressed from outside.

As illustrated in FIGS. 1A to 1C, microchannel chip 100 has chip main body (substrate) 110 and resin film 120.

Chip main body 110 is a substantially rectangular transparent resin substrate. Two through-holes 112a and 112b, and one bottomed recess 114 are formed in chip main body 110 (see FIGS. 2A to 2C). Two through-holes 112a and 112b constitute the bottomed recesses (first recess 170 and second recess 180), respectively, with resin film 120 closing one opening of both of through-holes 112a and 112b by resin film 120 (see FIG. 1B). Furthermore, recess 114 is the enclosed space (air reservoir 190) by closing the opening by resin film 120 (see FIG. 1C).

The shape of through-holes 112a and 112b, and recess 114 is not particularly limited and, for example, is substantially cylindrical shapes. The thickness of chip main body 110 is not particularly limited and, for example, is 1 mm to 10 mm. The diameter of through-hole 112a, 112b, and recess 114 is not particularly limited and, for example, is approximately 2 mm.

Grooves 116a, 116b and 116c connecting through-hole 112a and through-hole 112b with each other are formed on a surface of the resin film 120 side of chip main body 110. Grooves 116a, 116b and 116c constitute the channels (first channel 130, second channel 140 and communication section 150) connecting first recess 170 and second recess 180 with each other with resin film 120 closing the openings of grooves 116a, 116b and 116c at the resin film 120 side of chip main body 110 by resin film 120 (see FIG. 1B).

Furthermore, groove 116d connecting recess 114 and groove 116a with each other is formed on a surface of the resin film 120 side of chip main body 110. Groove 116d constitutes the channel (air introduction path 160) connecting air reservoir 190 and first channel 130 with each other with resin film 120 closing the opening of groove 116d by resin film 120 (see FIG. 1C).

Types of resin configuring chip main body (substrate) 110 are not particularly limited and are appropriately selected from publicly known resins. Examples of the resin configuring chip main body 110 include polyethylene terephthalate, polycarbonate, polymethyl methacrylate, vinyl chloride, polypropylene, polyether, polyethylene.

Resin film 120 is a substantially rectangular transparent resin film bonded to a surface of one side of chip main body 110 (see FIGS. 3A and 3B). For example, resin film 120 is bonded to chip main body 110 by thermal compression bonding. As described above, resin film 120 closes the openings of through-holes 112a and 112b, recess 114, and grooves 116a to 116d formed in chip main body 110.

The thickness of resin film 120 is not particularly limited and it is preferable that the thickness be formed such that a portion (a portion configuring a wall surface of air reservoir 190) closing the opening of recess 114 is deformed when being pressed from outside. Therefore, the capacity of air reservoir 190 can be reduced when the portion of resin film 120 is pressed from outside. For example, the thickness of resin film 120 is approximately 100 μm.

Types of resin configuring resin film 120 are not particularly limited and are appropriately selected from publicly known resins. Examples of the resin configuring resin film 120 are the same as the examples of the resin configuring chip main body 110. It is preferable that the resin configuring resin film 120 be the same as the resin configuring chip main body 110 from the viewpoint of improving adhesion between chip main body 110 and resin film 170.

As illustrated in FIG. 4, first channel 130 and second channel 140 are connected with each other through communication section 150. All of first channel 130, second channel 140 and communication section 150 are tubes through which a fluid can move by capillary action. Cross-sectional areas and cross-sectional shapes of first channel 130 and second channel 140 are not particularly limited as long as the fluid can move on the insides thereof by the capillary action. For example, the cross-sectional shapes of first channel 130 and second channel 140 are substantially rectangular shapes in which the dimension (width or depth) of one side thereof is approximately several tens of μm. As used herein, "cross-section of the channel" means a cross-section of the channel perpendicular to a direction in which a fluid flows.

On the other hand, the cross-sectional area of communication section 150 is sufficiently smaller than the cross-sectional area of second channel 140. More specifically, in a connection section between communication section 150 and second channel 140, the cross-sectional area of communication section 150 is smaller than the cross-sectional area of second channel 140, and the cross-sectional area of the channel is rapidly changed, for example, so that a difference is formed in the connection section. Therefore, the fluid inside communication section 150 cannot enter second channel 140 by its own surface tension. That is, the connection section between communication section 150 and second channel 140 serves as a valve. For example, the cross-sectional shape of communication section 150 is a substantially rectangular shape in which the dimension (width or depth) of one side is approximately 30 μm.

Furthermore, as illustrated in FIG. 4, air reservoir 190 is an enclosed space only communicating with air introduction path 160. As used herein, "enclosed space" means a space not directly communicating with outside. Air introduction path 160 communicates with first channel 130. Accordingly, when the atmospheric pressure in air reservoir 190 is increased, the air inside air reservoir 190 is introduced into first channel 130 through air introduction path 160.

As described above, air reservoir 190 is formed such that the capacity thereof decrease when resin film 120 configuring the wall surface of air reservoir 190 is pressed from outside. Accordingly, when the portion, facing to air reservoir 190, of resin film 120 is pressed from outside, the air inside air reservoir 190 is introduced into first channel 130 through air introduction path 160.

Microchannel chip 100 of the embodiment is manufactured by bonding chip main body 110 illustrated in FIGS. 2A to 2C and resin film 120 illustrated in FIGS. 3A and 3B.

Using Method of Microchannel Chip

Figure 5A:
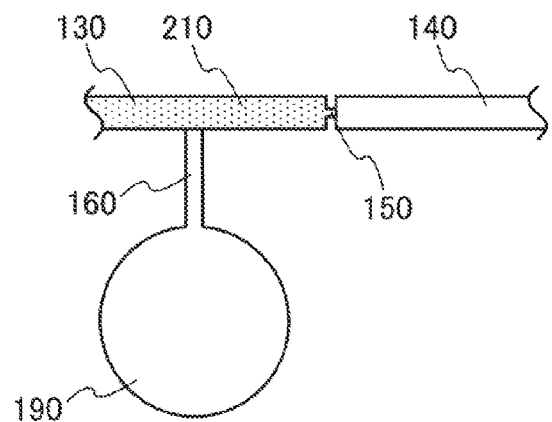
FIGS. 5A to 5C are partially enlarged plan views of the microchannel chip for describing a using method of the microchannel chip.
Figure 5B:
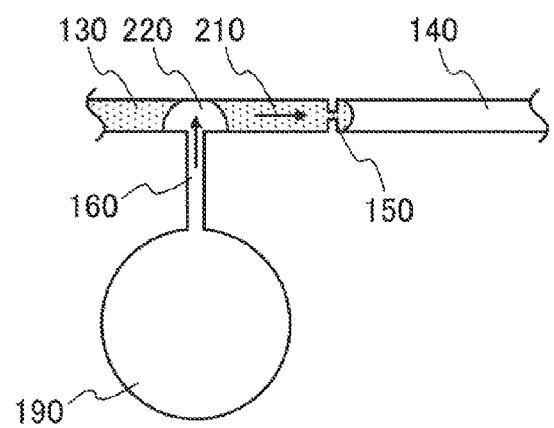
Figure 5C:
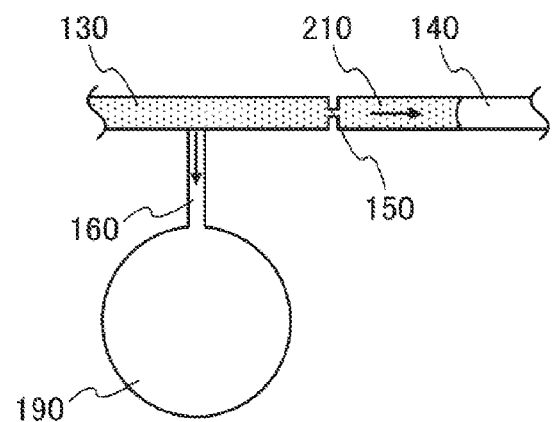

Next, a using method of microchannel chip 100 of the embodiment will be described with reference to FIGS. 5A to 5C. FIGS. 5A to 5C are partially enlarged plan views of microchannel chip 100 for describing a using mode of microchannel chip 100.

First, as illustrated in FIG. 5A, a liquid is introduced into first channel 130 and communication section 150 by supplying liquid 210 such as a reagent or a liquid sample to first recess 170. Liquid 210 inside first recess 170 advances into first channel 130 and communication section 150 by the capillary action and reaches the connection section between communication section 150 and second channel 140. As described above, since the connection section between communication section 150 and second channel 140 serves as the valve, liquid 210 cannot advance into second channel 140. Accordingly, the liquid can be introduced only into first channel 130 and communication section 150 by supplying liquid 210 to first recess 170. In addition, since air reservoir 190 does not communicate with outside, liquid 210 cannot advance into air introduction path 160.

Next, as illustrated in FIG. 5B, some of the air inside air reservoir 190 is introduced into first channel 130 through air introduction path 160 by pressing air reservoir 190 from outside. As a result, air bubble 220 is formed inside first channel 130. Some of liquid 210 inside first channel 130 and communication section 150 is pushed into second channel 140 from communication section 150 by air bubble 220.

As illustrated in FIG. 5B, when liquid 210 advances into second channel 140 beyond the connection section between communication section 150 and second channel 140, the connection section between communication section 150 and second channel 140 does not serve as the valve. Thus, as illustrated in FIG. 5C, when pressure on air reservoir 190 is stopped, liquid 210 can advance into second channel 140 by the capillary action. As described above, even though pressure on air reservoir 190 is stopped, liquid 210 moves inside of second channel 140 by the capillary action.

By the procedure described above, it is possible to allow liquid 210 to be retained inside first channel 130 and communication section 150, and liquid 210 inside first channel 130 and communication section 150 to move into second channel 140 at any intended timing. For example, after liquid 210 is reacted with a specific reagent inside first channel 130 for a certain period of time, liquid 210 inside first channel 130 moves into second channel 140, and then liquid 210 can be reacted with another reagent inside second channel 140.

Effect

In microchannel chip 100 of the embodiment, liquid 210 can be retained in first channel 130 and the communication section by the surface tension of liquid 210. In addition, in microchannel chip 100 of the embodiment, liquid 210 inside first channel 130 and the communication section can be moved to the into second channel 140 by pressing air reservoir 190 from outside. As described above, in microchannel chip 100 of the embodiment, the flow of the liquid inside the channels can be controlled easily without providing a large-scale apparatus (e.g.; pump, syringe) outside.

Modified Example

Figure 6A:
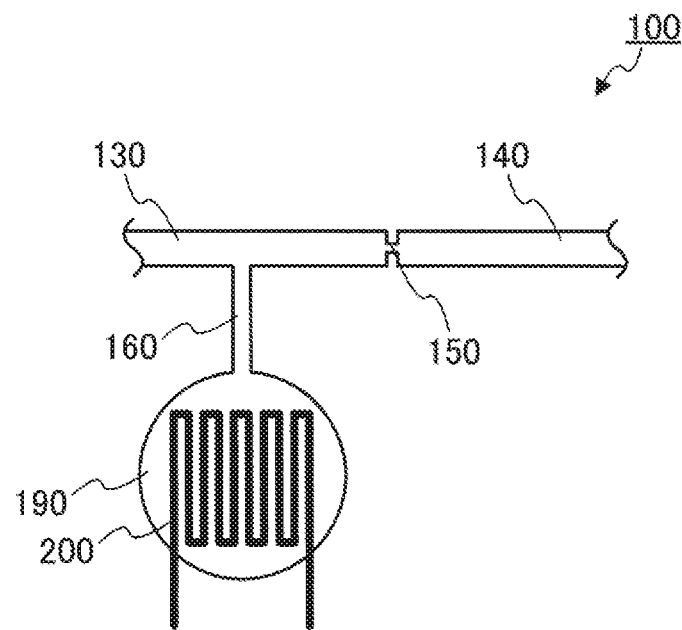
FIGS. 6A and 6B are partially enlarged plan views illustrating another example of the microchannel chip.

In the above description, an example is described in which the air inside air reservoir 190 is introduced into first channel 130 by pressing air reservoir 190 from outside; however, the method for introducing the air inside air reservoir 190 into first channel 130 is not limited to the example. For example, as illustrated in FIG. 6A, heating section 200 is disposed inside air reservoir 190 and the air inside air reservoir 190 may be heated. In this way, the air inside air reservoir 190 can be supplied to first channel 130.

Figure 6B:
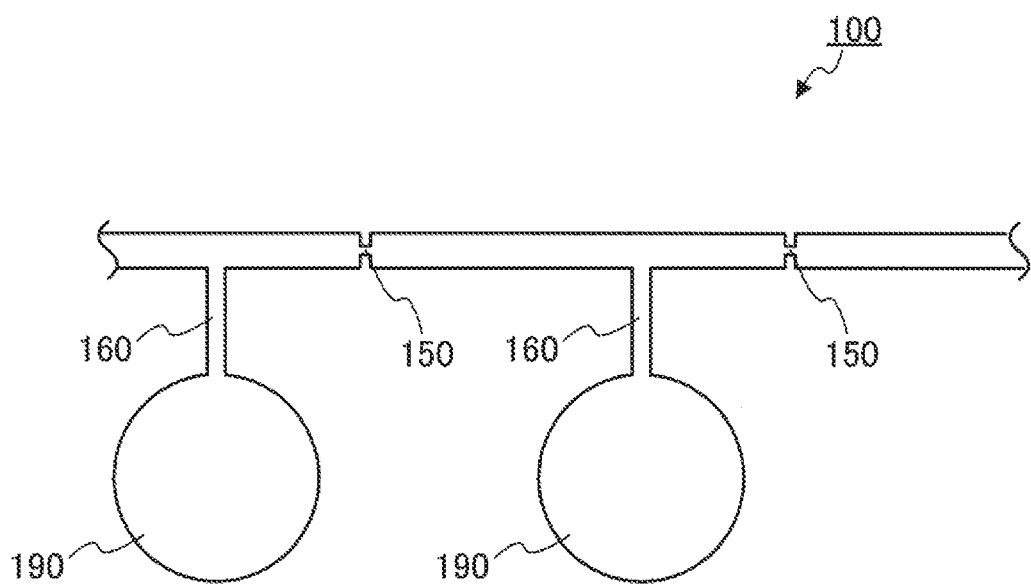

In the above description, microchannel chip 100 having one communication section 150 and one air reservoir 190 is described; however, the number of communication sections 150 and air reservoirs 190 inside microchannel chip 100 is not limited to the example. For example, as illustrated in FIG. 6B, a plurality of communication sections 150 and a plurality of air reservoirs 190 can be formed inside one microchannel chip 100.

Figure 7A:
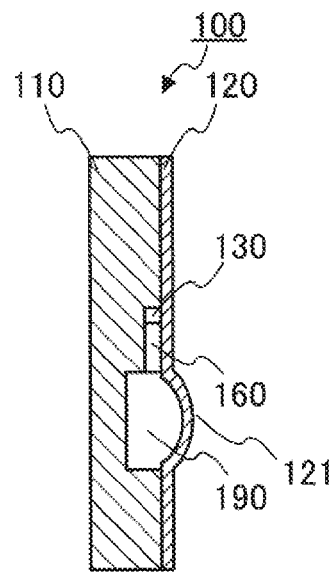
FIGS. 7A and 7B are cross-sectional views illustrating still another example of the microchannel chip.
Figure 7B:
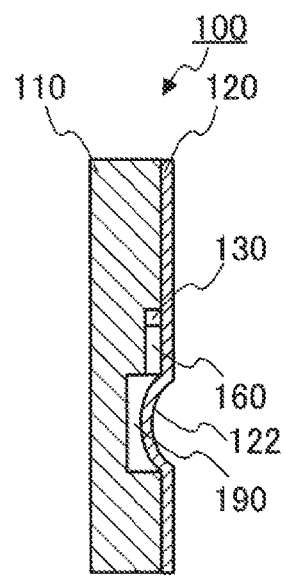

Air reservoir 190 is not limited to an example in which the wall surface thereof is configured of flat resin film 120. For example, as illustrated in FIG. 7A, the portion configuring the wall surface of air reservoir 190 in resin film 120 may be protrusion 121 which is protruded to outside in a dome shape. For example, protrusion 121 may be formed by bonding chip main body 110 and resin film 120 while sucking a portion configured to be the wall surface of air reservoir 190 in resin film 120. Therefore, as illustrated in FIG. 7B, recess 122 is formed and a pressing state (a state illustrated in FIG. 5B) of air reservoir 190 can be easily maintained by pressing protrusion 121 from outside. In addition, a certain amount of the air determined by the change of the shape of resin film 120 from protrusion 121 to recess 122 can be supplied to first channel 130. Thus, air bubble 220 of a certain size is formed inside first channel 130. Accordingly, specific volume of liquid 210 determined by the position of communication section 150 from the connection portion between first channel 130 and air introduction path 160, and the size of air bubble 220, can be scaled by supplying the air to first channel 130 by pressing protrusion 121.

Configuration of Fluid Handling System

Next, as a representative example of the fluid handling system of the present invention, the fluid handling system having the microchannel chip described above will be described.

Figure 8:
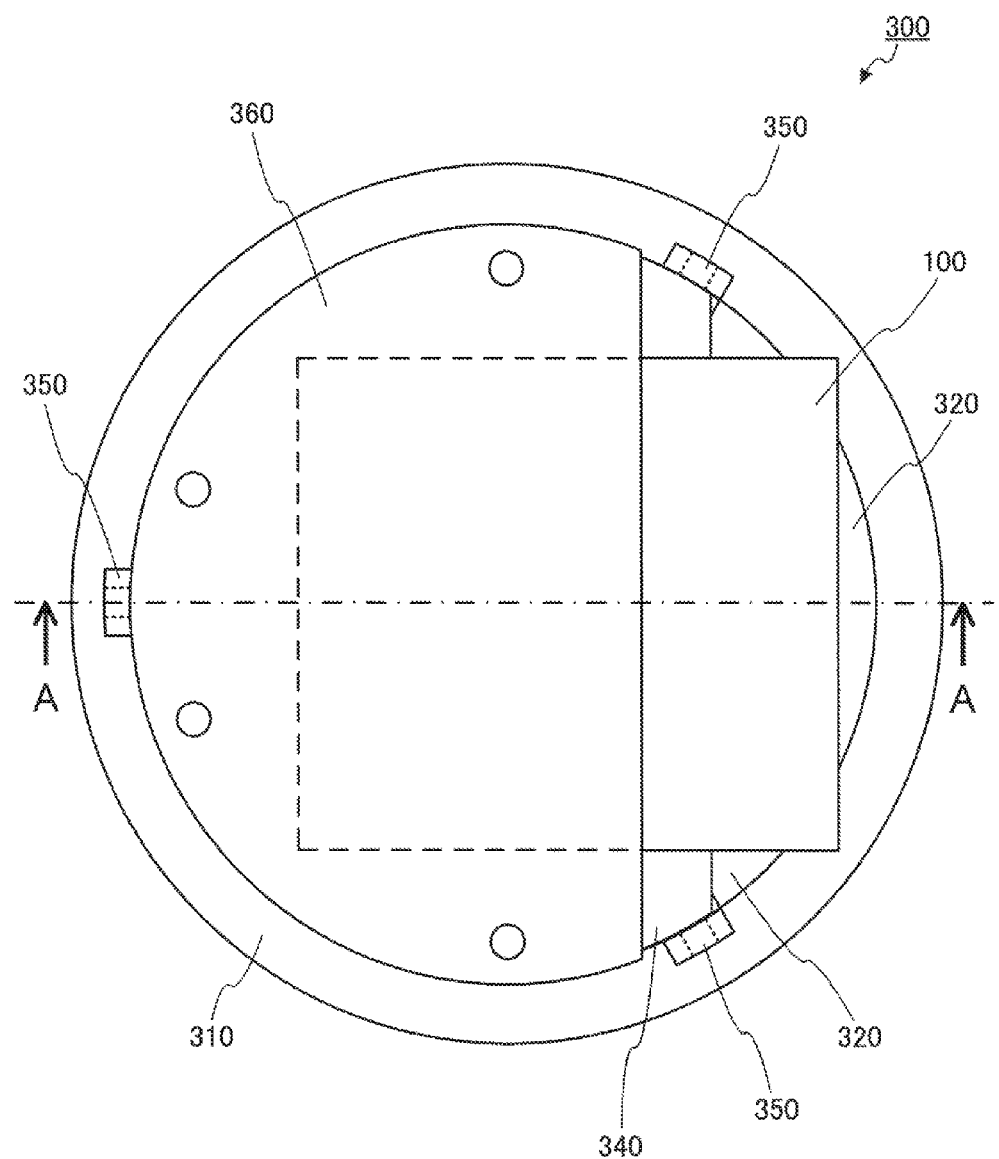
FIG. 8 is a plan view illustrating a configuration of a fluid handling system.
Figure 9:
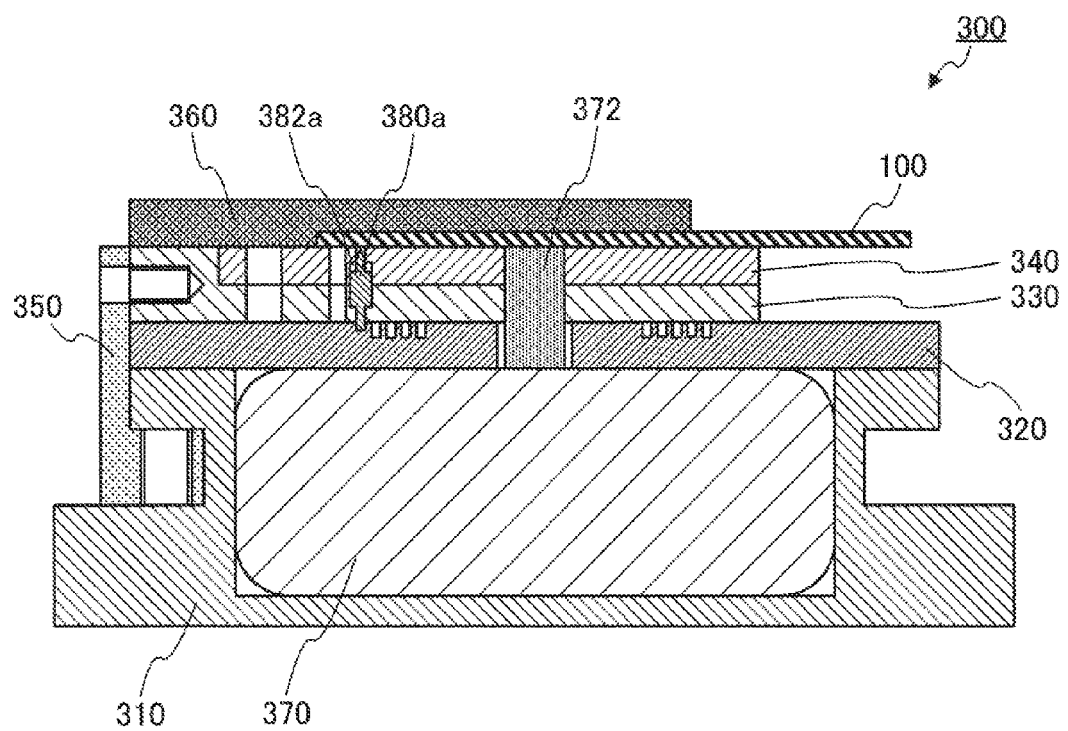
FIG. 9 is a cross-sectional view illustrating a configuration of the fluid handling system.

FIG. 8 is a plan view illustrating a configuration of fluid handling system 300 of the embodiment. FIG. 9 is a cross-sectional view of fluid handling system 300 taken along line A-A illustrated in FIG. 8. For example, the outer diameter of fluid handling system 300 is approximately 60 mm to 70 mm in a plan view.

Figure 10A:
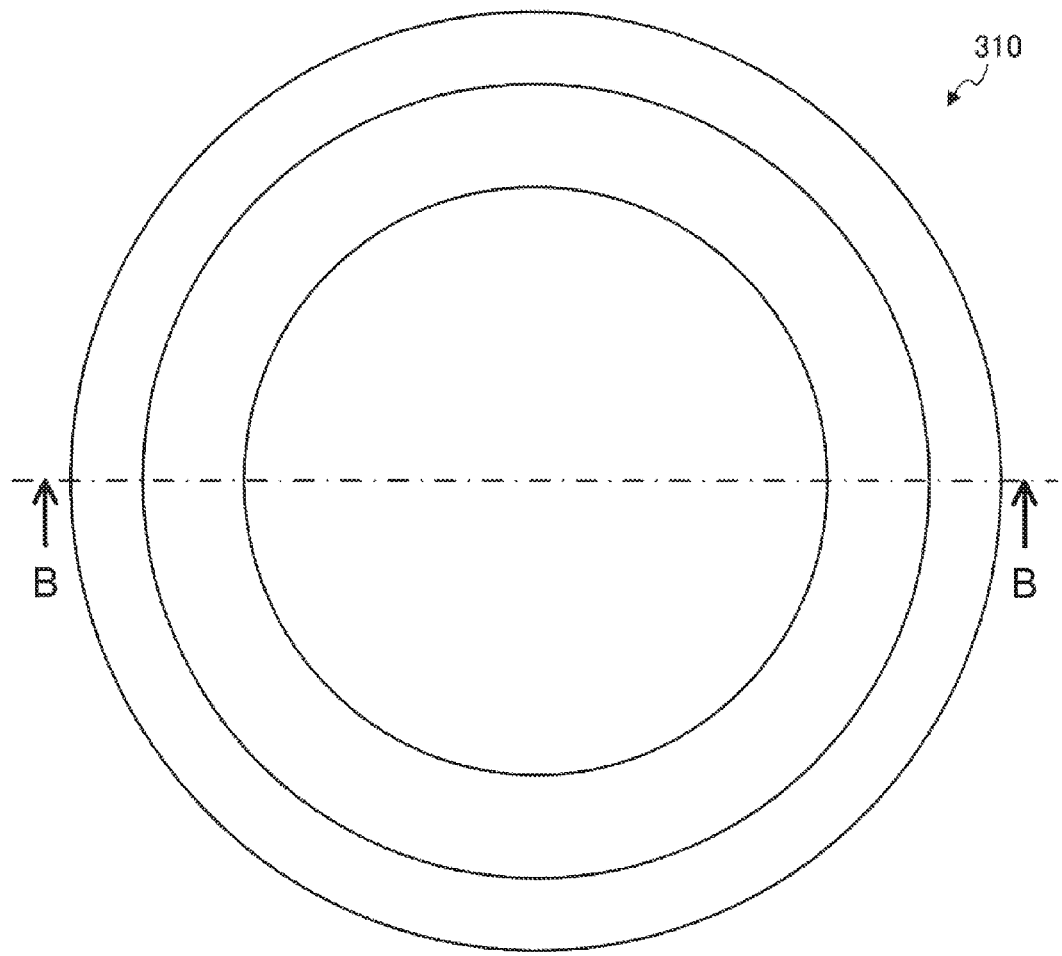
FIG. 10A is a plan view of a driving section holder and FIG. 10B is a cross-sectional view of the driving section holder taken along line B-B illustrated in FIG. 10A.
Figure 10B:
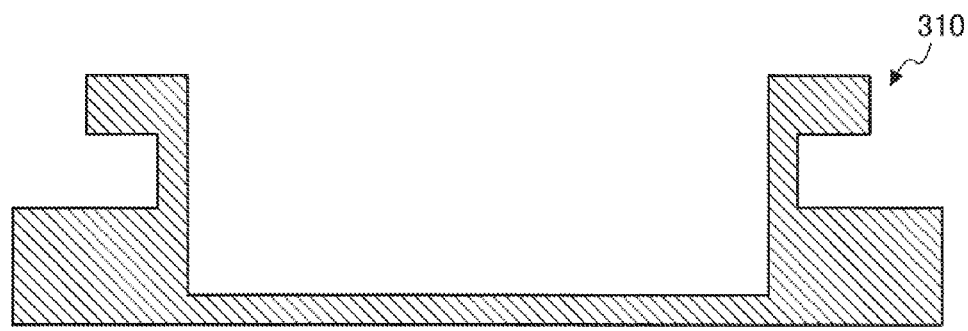

FIGS. 10A and 10B illustrate a configuration of driving section holder 310 of fluid handling system 300. FIG. 10A is a plan view of driving section holder 310 and FIG. 10B is a cross-sectional view of driving section holder 310 taken along line B-B illustrated in FIG. 10A.

Figure 11A:
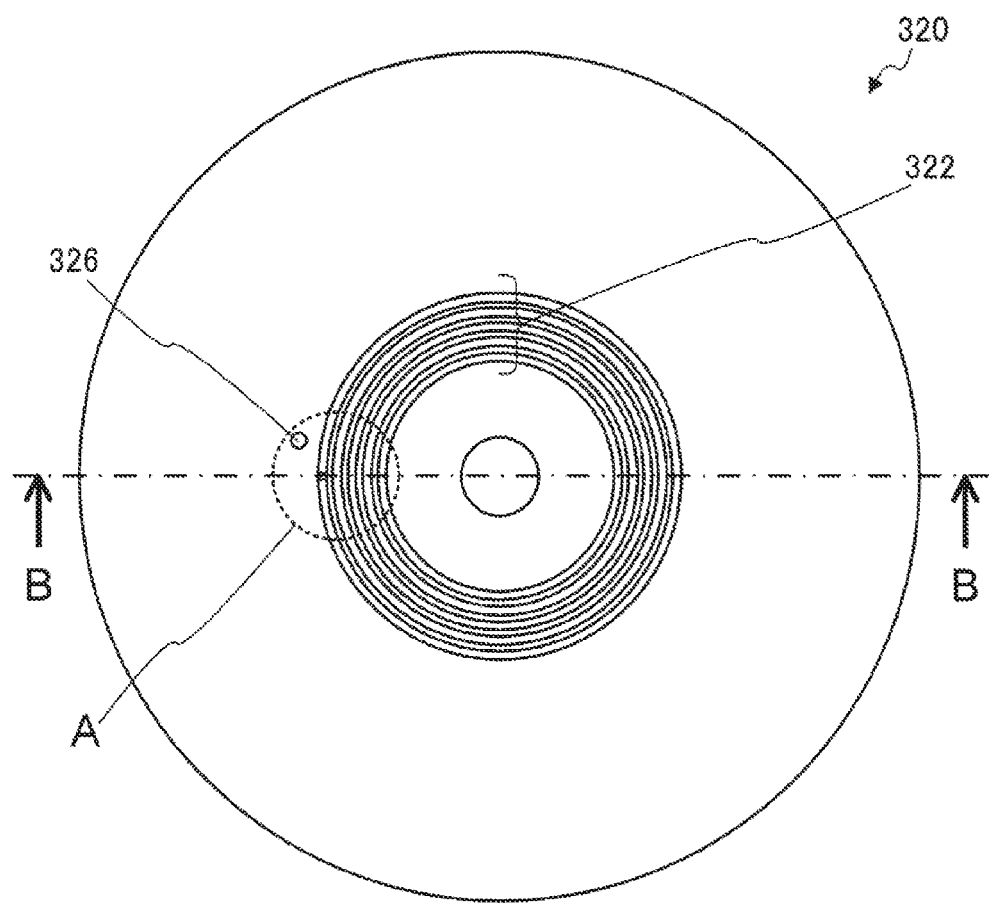
FIG. 11A is a plan view of a coded plate and FIG. 11B is a cross-sectional view of the coded plate taken along line B-B illustrated in FIG. 11A.
Figure 11B:
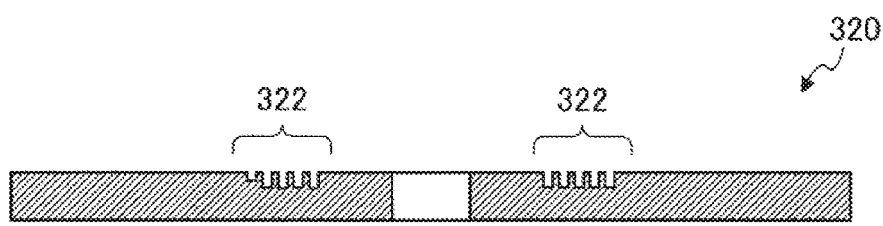

FIGS. 11A, 11B and 12A to 12D illustrate a configuration of coded plate 320 of fluid handling system 300. FIG. 11A is a plan view of coded plate 320 and FIG. 11B is a cross-sectional view of coded plate 320 taken along line B-B illustrated in FIG. 11A. FIG. 12A is an enlarged plan view of an area A indicated by a dashed line in FIG. 11A, FIG. 12B is a cross-sectional view of the area A taken along line B-B illustrated in FIG. 12A, FIG. 12C is a cross-sectional view of the area A taken along line C-C illustrated in FIG. 12A and FIG. 12B is a cross-sectional view of the area A taken along line D-D illustrated in FIG. 12A.

Figure 13A:
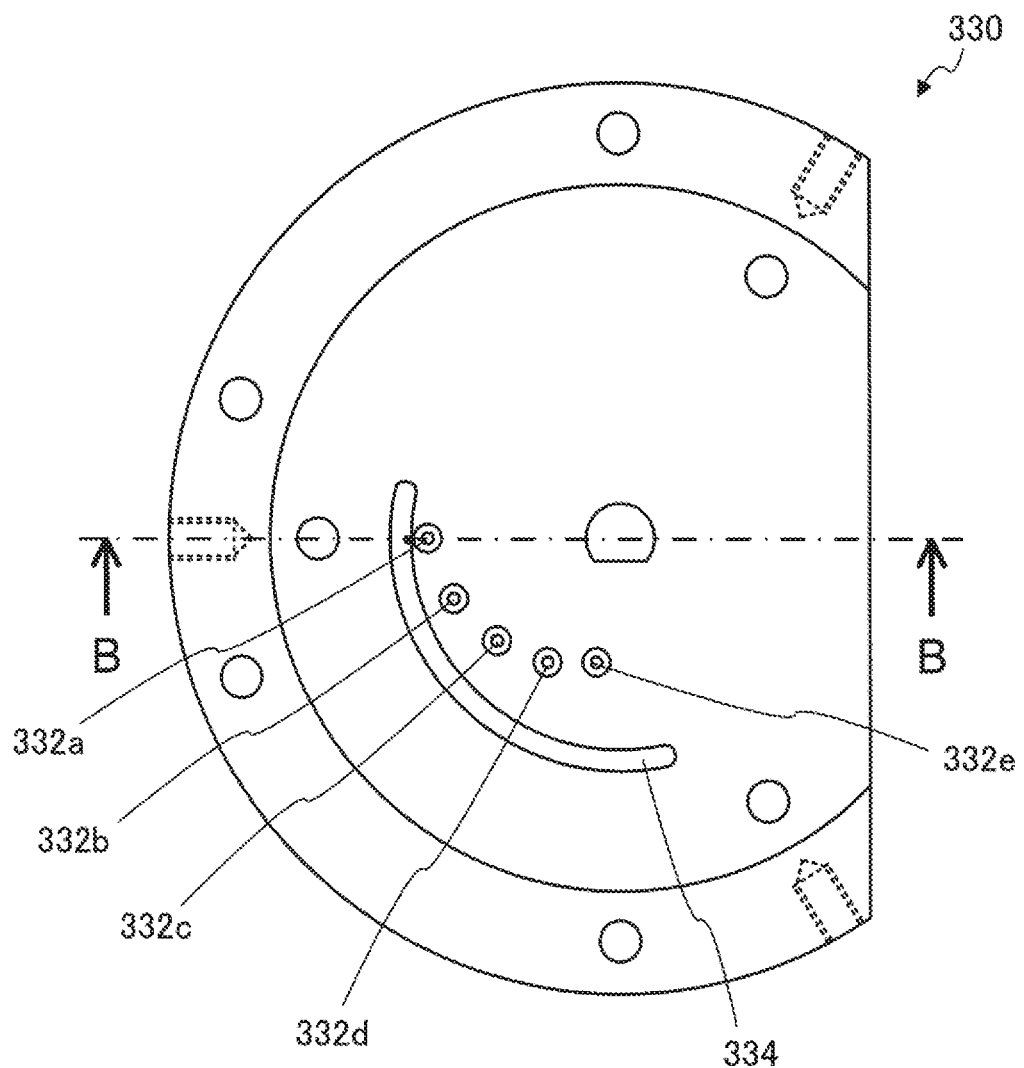
FIG. 13A is a plan view of a first pin holder and FIG. 13B is a cross-sectional view of the first pip holder taken along line B-B illustrated in FIG. 13A.
Figure 13B:
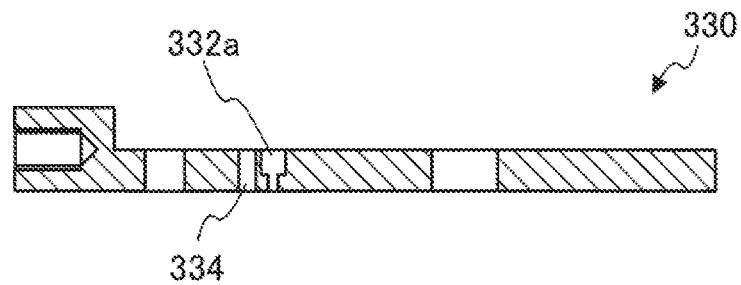

FIGS. 13A and 13B illustrate a configuration of first pin holder 330 of fluid handling system 300. FIG. 13A is a plan view of first pin holder 330 and FIG. 13B is a cross-sectional view of first pin holder 330 taken along line B-B illustrated in FIG. 13A.

Figure 14A:
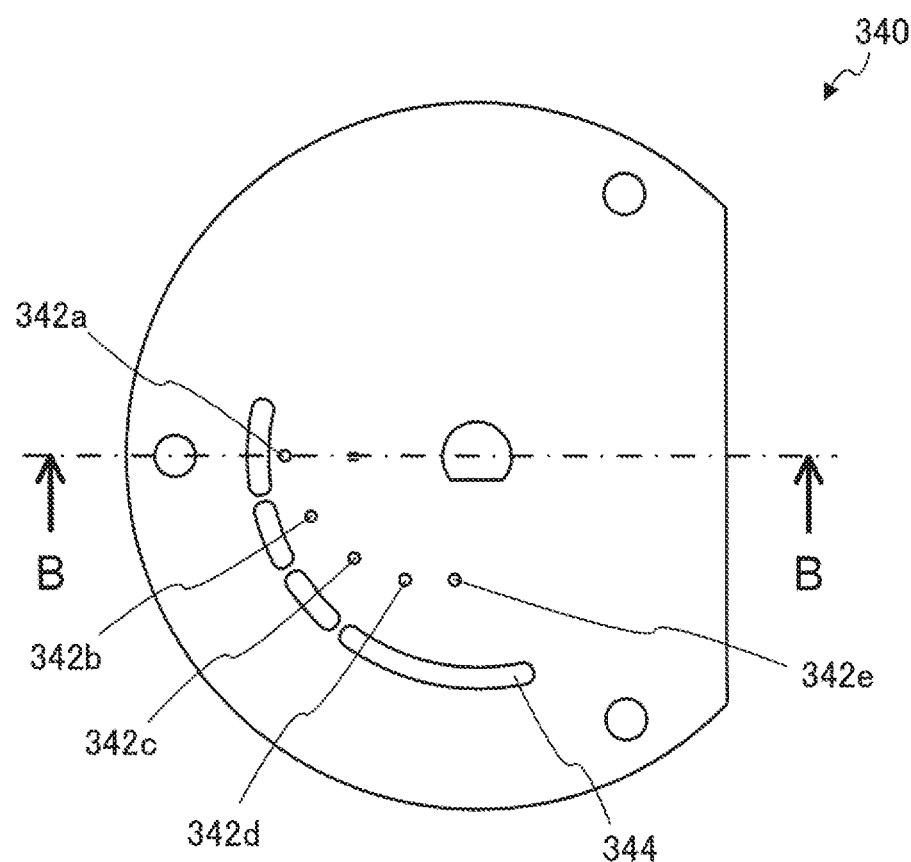
FIG. 14A is a plan view of a second pin holder and FIG. 14B is a cross-sectional view of the second pin holder taken along line B-B illustrated in FIG. 14A.
Figure 14B:
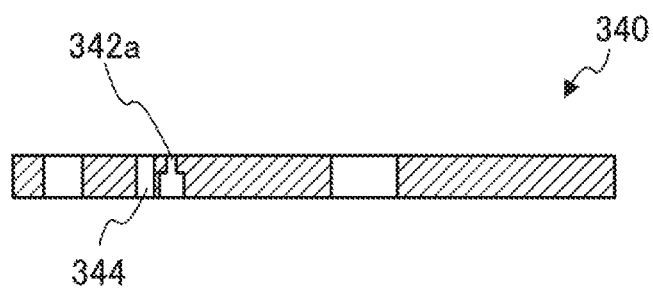

FIGS. 14A and 14B illustrate a configuration of second pin holder 340 of fluid handling system 300. FIG. 14A is a plan view of second pin holder 340 and FIG. 14B is a cross-sectional view of second pin holder 340 taken along line B-B illustrated in FIG. 14A.

Figure 15A:
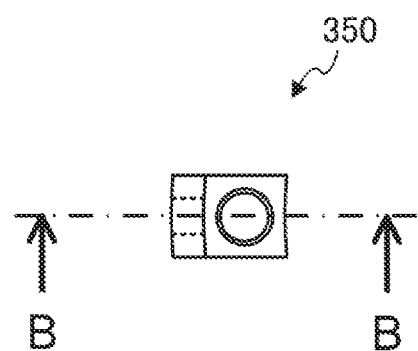
FIG. 15A is a plan view of a third pin holder and FIG. 15B is a cross-sectional view of the third pin holder taken along line B-B illustrated in FIG. 15A.
Figure 15B:
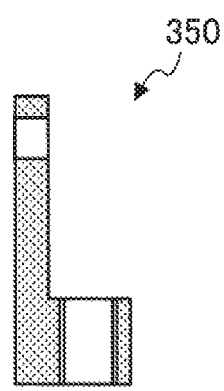

FIGS. 15A and 15B illustrate a configuration of third pin holder 350 of fluid handling system 300. FIG. 15A is a plan view of third pin holder 350 and FIG. 15B is a cross-sectional view of third pin holder 350 taken along line B-B illustrated in FIG. 15A.

Figure 16A:
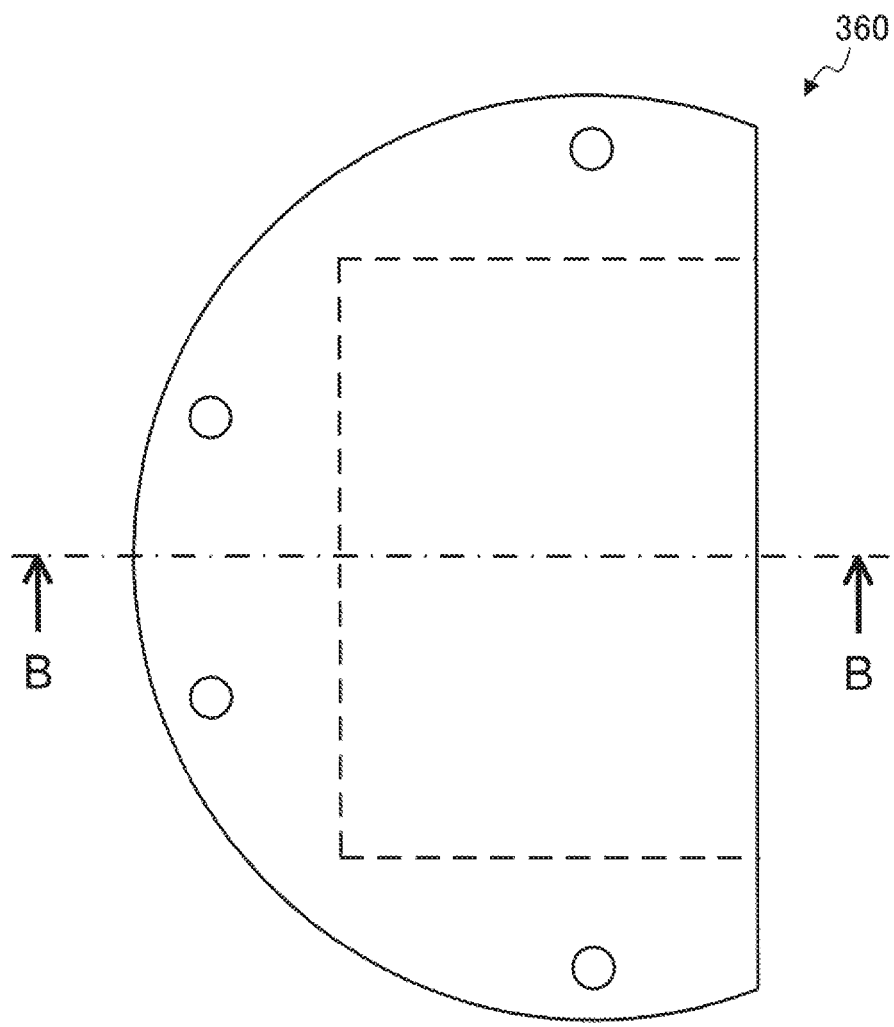
FIG. 16A is a plan view of a chip holder and FIG. 16B is a cross-sectional view of the chip holder taken along line B-B illustrated in FIG. 16A.
Figure 16B:
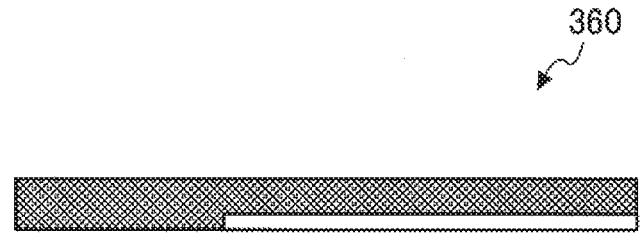

FIGS. 16A and 16B illustrate a configuration of chip holder 360 of fluid handling system 300. FIG. 16A is a plan view of chip holder 360 and FIG. 16B is a cross-sectional view of chip holder 360 taken along line B-B illustrated in FIG. 16A.

As illustrated in FIGS. 8 and 9, fluid handling system 300 of the embodiment has driving section holder 310, coded plate 320, first pin holder 330, second pin holder 340, third pin holder 350, chip holder 360, driving section 370 and a plurality of pins 380a to 380e (pins 380b to 380e are not illustrated). Fluid handling system 300 is used with microchannel chip 100 being inserted into a recess formed in chip holder 360.

Driving section holder 310 is a support member which supports driving section 370 and other members (see FIG. 9). A recess for installing driving section 370 is formed at a center portion of driving section holder 310. Furthermore, a groove where a protrusion of third pin holder 350 can be fitted is formed in an outer periphery of driving section holder 310 (see FIG. 10B).

Driving section 370 is disposed inside the recess of driving section holder 310. Driving section 370 operates fluid handling system 300 by rotating shaft 372 at a predetermined speed. As described below, first pin holder 330 and second pin holder 340 are fixed to rotating shaft 372. When rotating shaft 372 of driving section 370 is rotated, first pin holder 330, second pin holder 340, third pin holder 350, chip holder 360, a plurality of pins 380a to 380e and microchannel chip 100 are integrally rotated. For example, driving section 370 is electric machinery (motor), a flat spiral spring or the like.

Coded plate 320 is disposed on driving section holder 310 and is fixed by third pin holder 350. Coded plate 320 is not fixed to rotating Shaft 372 and coded plate 320 is not rotated even though rotating shaft 372 is rotated.

Five circumferential grooves 322a to 322e are formed on a surface of coded plate 320 (see FIGS. 11A and 11B). All of the centers of circumferential grooves 322a to 322e and the center of rotating shaft 372 coincide with one another.

Protrusion 324 is formed in each of grooves 322a to 322e (see FIGS. 12A to 12D). As described below, protrusion 324 defines operation contents of fluid handling system 300. That is, information defining the operation contents of fluid handling system 300 is written in grooves 322a to 322e of coded plate 320.

First pin holder 330 and second pin holder 340 are disposed on coded plate 320. On the other hand, third pin holder 350 is disposed on side surfaces of coded plate 320, first pin holder 330 and second pin holder 340. First pin holder 330, second pin holder 340 and third pin holder 350 are fixed to each other by screws not illustrated). In addition, first pin holder 330 and second pin holder 340 fixed to each other are fixed to rotating shaft 372. Therefore, when rotating shaft 372 is rotated, first pin holder 330, second pin holder 340 and third pin holder 350 are integrally rotated.

Through-holes 332a to 332e for accommodating pins 380a to 380e are formed in first pin holder 330 (see FIG. 13A). Similarly, through-holes 342a to 342e for accommodating pins 380a to 380e are also formed in second pin holder 340 (see FIG. 14A). When first pin holder 330 and second pin holder 340 are fixed to rotating shaft 372, through-hole 332a and through-hole 342a together form one pin accommodation section 382a (see FIG. 9). Similarly, through-holes 332b to 332e and through-holes 342b to 342e also form pin accommodation sections 382b to 382e, respectively. Pin accommodation sections 382a to 382e formed as described above are positioned on grooves 322a to 322e of coded plate 320, respectively.

Pins 380a to 380e are housed inside pin accommodation sections 382a to 382e (see FIG. 9). Lower ends of pins 380a to 380e come into contact with bottom surfaces of grooves 322a to 322e of coded plate 320, respectively. Upper ends of pins 380a to 380e face resin film 120 (a portion configuring the wall surface of air reservoir 190) of microchannel chip 100, respectively.

Chip holder 360 is fixed on first pin holder 330 and second pin holder 340. A recess for inserting microchannel chip 100 is formed on a surface of second pin holder 340 side of chip holder 360 (see FIGS. 16A and 16B).

Operation of Fluid Handling System

Next an operation of fluid handling system 300 of the embodiment will be described with reference to FIG. 17. FIG. 17 is a partially enlarged cross-sectional view of fluid handling system 300 for describing the operation of fluid handling system 300.

When driving section 370 rotates rotating shaft 372 at a predetermined speed, first pin holder 330, second pin holder 340, third pin holder 350, chip holder 360, pins 380a to 380e and microchannel chip 100 are integrally rotated. On the other hand, coded plate 320 is not rotated. Therefore, pins 380a to 380e move in such a manner as to trace grooves 322a to 322e of coded plate 320, respectively.

Figure 17A:
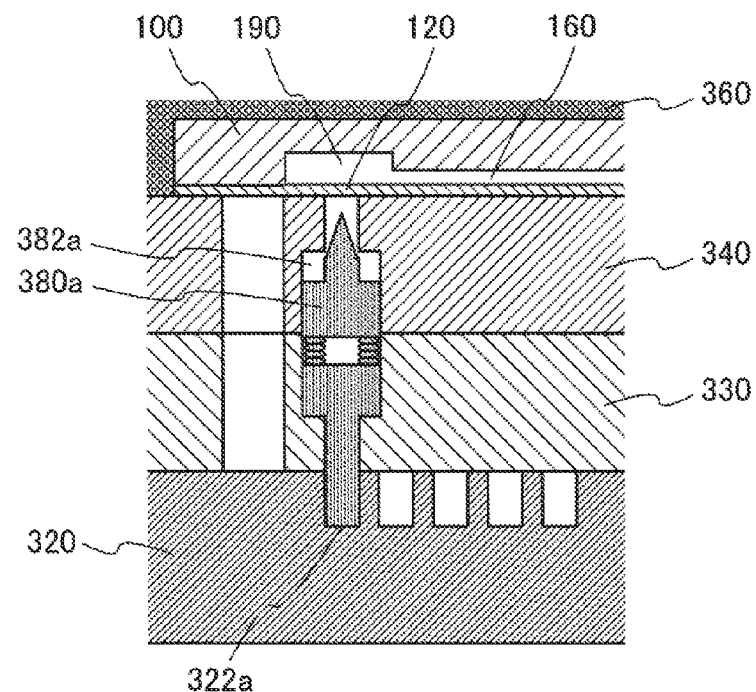
FIGS. 17A and 17B are partially enlarged cross-sectional views of the fluid handling system for describing operation of the fluid handling system.
Figure 17B:
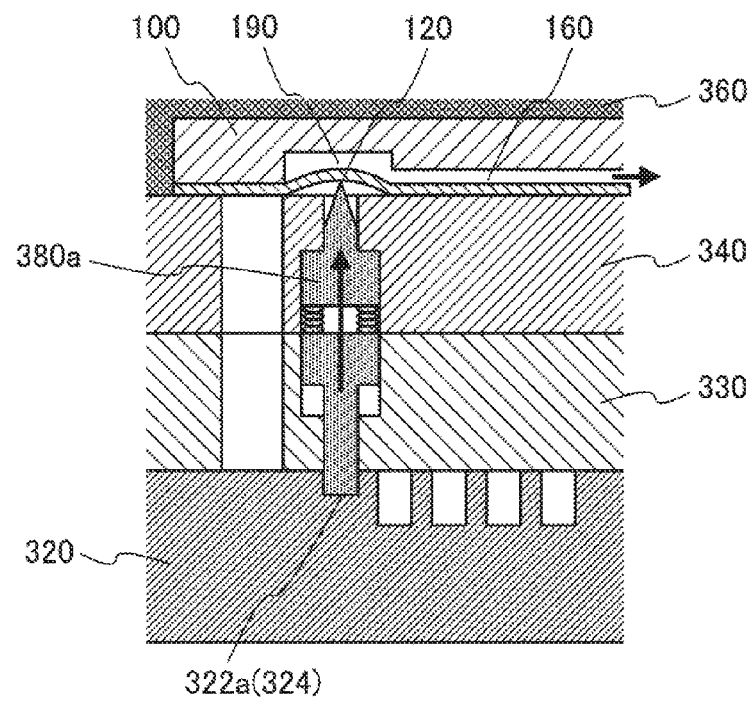

As illustrated in FIG. 17A, when grooves 322a to 322e have normal depths, the upper ends of pins 380a to 380e do not come into contact with resin film 120 of microchannel chip 100. On the other hand, as illustrated in FIG. 17B, when the lower ends of pins 380a to 380e ride on protrusions 324 of grooves 322a to 322e, the upper ends of pins 380a to 380e press resin film 120 of microchannel chip 100. Therefore, the air inside air reservoir 190 is introduced into first channel 130 through air introduction path 160 and liquid 210 inside first channel 130 is introduced into second channel 140.

As described above, in fluid handling system 300 of the embodiment, pins 380a to 380e automatically press resin film 120 of microchannel chip 100 depending on patterns of protrusion 324 formed in grooves 322a to 322e of coded plate 320. Therefore, a micro-valve (a micro-valve configured of first channel 130, second channel 140, communication section 150, air introduction path 160 and air reservoir 190) of microchannel chip 100 is automatically open depending on patterns of protrusion 324 formed in grooves 322a to 322e of coded plate 320.

Effect

In fluid handling system 300 of the embodiment, it is possible to automatically open the micro-valve provided inside microchannel chip 100 at any intended timing. In fluid handling system 300 of the embodiment, since it is not necessary to provide a large-scale apparatus (e.g.; pump, syringe), fluid handling system 300 can be easily downsized.

In addition, when heating section 200 is disposed inside air reservoir 190 of microchannel chip 100 (sec FIG. 6A), fluid handling system 300 may open the micro-valve of microchannel chip 100 by heating air inside air reservoir 190. That is, a valve opening portion provided in fluid handling system 300 may open the micro-valve by pressing air reservoir 190 of microchannel chip 100 from outside, and may open the micro-valve by heating the air inside air reservoir 190.

Furthermore, in the above description, an example is described in which pins 380a to 380e are operated using protrusion 324 formed in grooves 322a to 322e of coded plate 320; however, the method for operating pins 380a to 380e is not limited to the example. For example, pins 380a to 380e may be operated using a leaf spring, a solenoid actuator, a pneumatic cylinder or the like.

Furthermore, when liquid 210 introduced into microchannel chip 100 includes magnetic beads, a magnet is provided in fluid handling system 300 of the embodiment, so that the magnetic beads can be operated. For example, it is possible to perform purification or separation of specific biotin-labeled molecules inside liquid 210 by operating the magnetic beads on which streptavidin is immobilized using the magnet fitted in hole portion 326 of coded plate 320, groove 334 of first pin holder 330 and groove 344 of second pin holder 340 (by moving or accumulating the magnetic beads inside first channel 130 and second channel 140).

This application claims priority based on Japanese patent Application No. 2011-155679, filed on Jul. 14, 2011. The contents described in the application specification and the drawings are all incorporated herein.

INDUSTRIAL APPLICABILITY

The fluid handling device of the present invention is, for example, useful as a micro-chip or a microchannel chip which is used in a scientific field, a medical field or the like. Furthermore, the fluid handling system of the present invention is, for example, useful as a system for performing accurate and fast analysis of a very small amount of a material.

REFERENCE SIGNS LIST

100 Microchannel chip
110 Chip main body
112a, 112b Through-hole
114 Recess
116a to 116d Groove
120 Resin film
130 First channel
140 Second channel
150 Communication section
160 Air introduction path
170 First recess
180 Second recess
190 Air reservoir
200 Heating section
210 Liquid
220 Air bubble
300 Fluid handling system
310 Driving section holder
320 Coded plate
322a to 322e Groove
324 Protrusion
326 Hole portion
330 First pin holder
332a to 332e Through-hole
334 Groove
340 Second pin holder
342a to 342e Through-hole
344 Groove
350 Third pin holder
360 Chip holder
370 Driving section
372 Rotating shaft
380a Pin
382a to 382e Pin accommodation section

The invention claimed is:
1. A fluid handling device comprising:
an introduction port;
a first channel through which a fluid can move by capillary action, the first channel being connected to the introduction port and the introduction port introduces the fluid into the first channel;

a second channel through which the fluid can move by the capillary action;

a communication section that is a channel through which the fluid can move by the capillary action, the communication section connecting the first channel and the second channel with each other, and having a cross-sectional area smaller than a cross-sectional area of each of the first channel and the second channel;

an air introduction path connected to the first channel at a position which is closer to the communication section than the introduction port; and an air reservoir connected to the air introduction path, wherein the air reservoir comprises:
- a reservoir housing having a recess which has an opening located on a bottom surface of the housing, and
- a resin film covering the bottom surface, wherein a portion of the resin film which covers the opening, has a shape retention property and is configuring a wall surface of the air reservoir, is protruding towards outside to thereby form a protrusion in a retentive dome shape and keeps a concave shape by being pressed from the outside.

2. A fluid handling method in which a fluid is handled using the fluid handling device according to claim 1, comprising:
introducing the fluid into the first channel and the communication section;
pushing some of the fluid inside the first channel and the communication section to the second channel by pushing a volume of air inside the air reservoir toward the first channel through the air introduction path; and
moving the fluid in the second channel by the capillary action.

3. The fluid handling method according to claim 2, wherein
a volume of air inside the air reservoir is pushed toward the first channel by pressing the air reservoir from outside.

4. A fluid handling system comprising:
the fluid handling device according to claim 1; and
a valve opening portion that presses the air reservoir of the fluid handling device from outside.

* * * * *